US009345890B2

(12) United States Patent
Saha et al.

(10) Patent No.: US 9,345,890 B2
(45) Date of Patent: May 24, 2016

(54) SYSTEMS AND METHODS FOR MANAGING NOISE IN IMPLANTABLE MEDICAL DEVICES

(75) Inventors: Sunipa Saha, Shoreview, MN (US); Eric K. Enrooth, Lino Lakes, MN (US); Scot C. Boon, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 421 days.

(21) Appl. No.: 12/815,871

(22) Filed: Jun. 15, 2010

(65) Prior Publication Data

US 2010/0318151 A1 Dec. 16, 2010

Related U.S. Application Data

(60) Provisional application No. 61/187,096, filed on Jun. 15, 2009.

(51) Int. Cl.
*A61N 1/37* (2006.01)
*A61B 5/0428* (2006.01)
(Continued)

(52) U.S. Cl.
CPC .............. *A61N 1/371* (2013.01); *A61B 5/0428* (2013.01); *A61B 5/0432* (2013.01); *A61B 5/7203* (2013.01); *A61B 5/7217* (2013.01);
(Continued)

(58) Field of Classification Search
CPC ... A61N 1/36128; A61N 1/37; A61N 1/3702; A61N 1/3704; A61N 1/371; A61N 1/3712; A61N 1/3714; A61N 1/3925
USPC ........................................................ 607/2–18
See application file for complete search history.

(56) References Cited

U.S. PATENT DOCUMENTS 4,562,841 A 1/1986 Brockway et al.
4,969,464 A 11/1990 Callaghan et al.
(Continued)

FOREIGN PATENT DOCUMENTS

JP 5680634 1/2015
WO 01097059 3/2003
WO 2005018738 3/2005

OTHER PUBLICATIONS

"PCT International Search Report and Written Opinion", from International Application No. PCT/US2010/038665, corresponding to U.S. Appl. No. 12/815,871, mailed Sep. 30, 2010, pp. 1-14.
(Continued)

*Primary Examiner* — Allen Porter, Jr.
(74) *Attorney, Agent, or Firm* — Schwegman Lundberg & Woessner, P.A.

(57) ABSTRACT

Embodiments of the invention are related to managing noise in sensed signals in implantable medical devices, amongst other things. In an embodiment the invention includes a method for processing electrical signals obtained from a patient including gathering a first set of electrical signals using an implantable medical device, filtering to provide a second set of electrical signals, the second set including frequencies above a threshold frequency, and estimating the amount of noise present in the first set of electrical signals based on the magnitude of the second set. In an embodiment, the invention includes a medical device configured to gather a first set of electrical signals, filter the first set to provide a second set of electrical signals including frequencies above a threshold frequency, and estimate the amount of noise present in the first set based on the magnitude of the second set. Other embodiments are also included herein.

17 Claims, 7 Drawing Sheets

(51) Int. Cl.
*A61B 5/0432* (2006.01)
*A61B 5/00* (2006.01)
*G06K 9/00* (2006.01)

(52) U.S. Cl.
CPC ............. *G06K9/0051* (2013.01); *A61N 1/3714* (2013.01); *A61N 1/3718* (2013.01)

(56) References Cited

U.S. PATENT DOCUMENTS

| | | | | |
|---|---|---|---|---|
| 5,443,485 | A * | 8/1995 | Housworth et al. | 607/28 |
| 5,690,685 | A * | 11/1997 | Kroll et al. | 607/5 |
| 6,041,250 | A | 3/2000 | DePinto et al. | |
| 6,263,238 | B1 * | 7/2001 | Brewer et al. | 607/5 |
| 6,505,071 | B1 | 1/2003 | Zhu et al. | |
| 6,917,830 | B2 | 7/2005 | Palreddy et al. | |
| 7,155,275 | B2 | 12/2006 | Linder et al. | |
| 7,215,993 | B2 | 5/2007 | Lin | |
| 2002/0120303 | A1 * | 8/2002 | Levine | A61N 1/3622 607/14 |
| 2003/0050671 | A1 * | 3/2003 | Bradley | A61N 1/3712 607/27 |
| 2003/0187337 | A1 | 10/2003 | Tarassenko et al. | |
| 2004/0082975 | A1 * | 4/2004 | Meyer | A61N 1/3712 607/27 |
| 2004/0127951 | A1 * | 7/2004 | Jarverud | A61N 1/368 607/27 |
| 2004/0260351 | A1 * | 12/2004 | Holmstrom | A61N 1/3712 607/27 |
| 2005/0192504 | A1 * | 9/2005 | Palreddy et al. | 600/509 |
| 2006/0085038 | A1 * | 4/2006 | Linder et al. | 607/4 |
| 2006/0247695 | A1 * | 11/2006 | Stalsberg et al. | 607/9 |
| 2007/0016261 | A1 * | 1/2007 | Dong et al. | 607/28 |
| 2007/0073347 | A1 * | 3/2007 | Corbucci | A61B 5/0006 607/9 |
| 2007/0129762 | A1 * | 6/2007 | Worley | 607/9 |
| 2007/0219453 | A1 | 9/2007 | Kremliovsky et al. | |
| 2010/0147983 | A1 | 6/2010 | Evans et al. | |

OTHER PUBLICATIONS

Clarke, Malcolm "Automatic Adjustment of Pacemaker Stimulation Output Correlated with Continuously Monitored Capture Thresholds: a Multicenter Study", *European Microny Study Group. Packing Clin. Electrophysiol*. Aug. 1998, 21:1567-75.

Kam, Ruth "Automatic Capture Verification in Pacemakers (Autocapture)—Utility and Problems", *Indian Pacing and Electrophysiology Journal* 2004, 4(2):73-78.

"International Preliminary Report on Patentability", from International Application No. PCT/US2010/038665, corresponding to U.S. Appl. No. 61/187,096, mailed Dec. 29, 2011, pp. 1-8 , 8.

"Office Action", from JP Application No. 2012-516200, mailed Oct. 16, 2013 (8 pages).

Non-Final Office Action, for JP Application No. 2012516200, mailed May 15, 2014 (7 pages).

"Notice of Allowance," for Japanese Patent Application No. 2012-516200, mailed Dec. 19, 2014 (3 pages).

"European Application Serial No. 10728499.4, Examination Notification Art, 94(3) mailed Jun. 30, 2015", 6 pgs.

"European Application Serial No. 10728499.4, Office Action mailed Mar. 7, 2012", 2 pgs.

"European Application Serial No. 10728499.4, Response filed Sep. 6, 2012 to Office Action mailed Mar. 7, 2012", 13 pgs.

* cited by examiner

SYSTEMS AND METHODS FOR MANAGING NOISE IN IMPLANTABLE MEDICAL DEVICES

This application claims the benefit of U.S. Provisional Application No. 61/187,096, filed Jun. 15, 2009, the content of which is herein incorporated by reference in its entirety.

TECHNICAL FIELD

This disclosure relates generally to implantable medical devices, and more particularly, systems and methods for managing noise in sensed signals in implantable medical devices, amongst other things.

BACKGROUND OF THE INVENTION

Implantable medical devices (IMDs) are commonly used to provide treatment to patients. Implantable medical devices can include cardiac rhythm management devices and neurological stimulation devices, amongst others. Some types of implantable medical devices deliver electrical stimuli to a target tissue via a lead wire ("stimulation lead") or catheter having one or more electrodes disposed in or about the target tissue.

In many scenarios, implantable medical devices are configured to sense electrical activity in vivo. By way of example, cardiac rhythm management devices frequently sense electrical activity of cardiac tissue in order to gather information about cardiac rhythm and the effect of therapeutic electrical stimulation.

Some implantable medical devices include features directed to automating the process of setting device parameters. By way of example, some implantable medical devices include what is known as an automatic threshold measurement test. This test automatically determines the minimum amplitude of electrical stimulation needed to cause a given chamber of the heart to contract. At a high level, this test involves stimulating at successively lower amplitudes and monitoring for contraction (an evoked response) until the amplitude becomes so low that contraction is no longer achieved in response to the stimulation. However, noise can limit the accuracy of such testing.

SUMMARY OF THE INVENTION

Embodiments of the invention are related to managing noise in sensed signals in implantable medical devices, amongst other things. In an embodiment the invention includes a method for processing electrical signals obtained from a patient. The method can include gathering a first set of electrical signals within the patient using an implantable medical device. The method can also include filtering to provide a second set of electrical signals from the first set of electrical signals, the second set of electrical signals including frequencies above a cutoff frequency. The method can also include estimating the amount of noise present in the first set of electrical signals based on the magnitude of the second set of electrical signals.

In an embodiment, the invention includes a medical device including a processor circuit and a memory circuit operatively connected to the processor circuit. The medical device can be configured to gather a first set of electrical signals from a patient. The medical device can further be configured to filter the first set of electrical signals to provide a second set of electrical signals, the second set of electrical signals including frequencies above a cutoff frequency. The medical device can further be configured to estimate the amount of noise present in the first set of electrical signals based on the magnitude of the second set of electrical signals.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Noise in sensed signals can inhibit the accuracy of algorithms used to control various aspects of device functionality. By way of example, noise can adversely impact the accuracy of automatic threshold tests that determine the minimum amplitude of electrical stimulation needed to cause a given chamber of the heart to contract.

Figure 1:
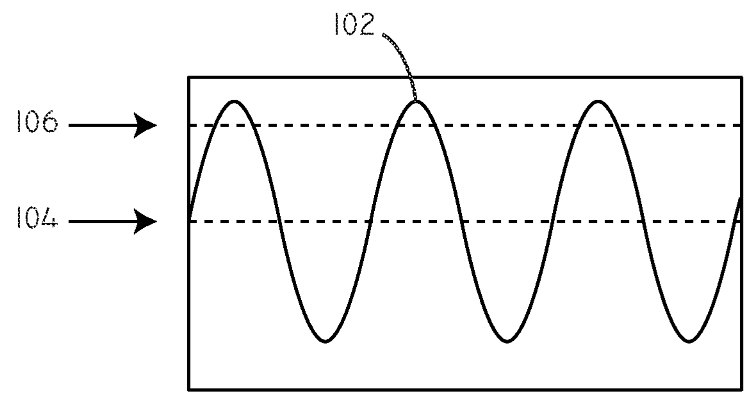
FIG. 1 is a graph of continuous noise at 60 Hz.

Noise in sensed signals can include various types. One type of noise is continuous noise at a constant frequency. FIG. 1 is a graph of idealized continuous noise at 60 Hz. In many cases, algorithms may use amplitude thresholds in order to determine whether or not contraction of a heart chamber has taken place. In some cases, multiple different thresholds can be used. In this illustration, there are two thresholds in place: a pace artifact threshold 104 and a capture detection threshold 106. The pace artifact threshold 104 can be used in some algorithms to help distinguish between loss of capture and fusion beats. Fusion beats are where an intrinsic depolarization of a particular chamber merges with a pacemaker output pulse within that chamber. The failure to sense an evoked response following a pacing stimulus may be due either to loss of capture or a fusion beat. In some embodiments of automatic threshold testing, sensed electrical signals that fail to exceed the pace artifact threshold 104 are identified as loss of capture beats. The capture (or evoked response) detection threshold 106 can be used in some algorithms to determine if contraction of a heart chamber has taken place. It will be appreciated that the absolute magnitude of the thresholds may vary in different implementations. However, regardless of the specific threshold magnitude, it is conceivable that the threshold could be triggered simply by noise.

Figure 2:
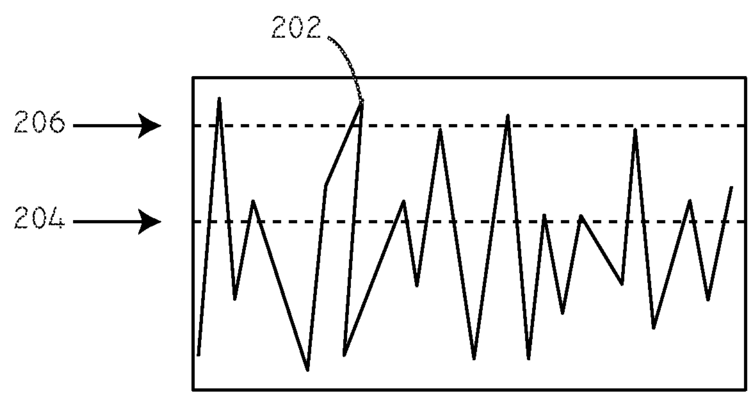
FIG. 2 is a graph of myopotential noise.

In the illustration of FIG. 1, the noise 102 is shown with an amplitude that at various points exceeds both the pace artifact threshold 104 and the capture detection threshold 106. Unfortunately, if the noise 102 exceeds the pace artifact threshold 104, then the system might not be able to accurately distinguish between loss of capture and fusion beats. Further, if the noise 102 exceeds the capture detection threshold 106, the device could erroneously indicate that contraction in a chamber of the heart has taken place. In the context of an automatic threshold test, this could lead to incorrect (higher or lower) pacing thresholds being set by the system. Beyond constant noise at a particular frequency, the contraction of muscle in the body also accounts for a substantial amount of noise. FIG. 2 is a graph of myopotential noise. Similar to as described with respect to FIG. 1, if the noise 202 exceeds the pace artifact threshold 204, the system cannot accurately distinguish between loss of capture and fusion beats. If the noise 202 exceeds the capture detection threshold 206, then depending on the particular algorithm being used, the device could erroneously indicate that contraction in a chamber of the heart has taken place.

Atrial signals, such as atrial electrogram signals, have relatively low amplitude in comparison with ventricular signals. As such, atrial capture detection thresholds are typically much closer to the levels of prevailing noise than would be true for ventricular capture thresholds. Therefore, it will be appreciated that although systems and methods included herein have broad applicability with respect to managing noise in all types of signals, the need for managing noise is particularly acute in the context of atrial signals.

Figure 3:
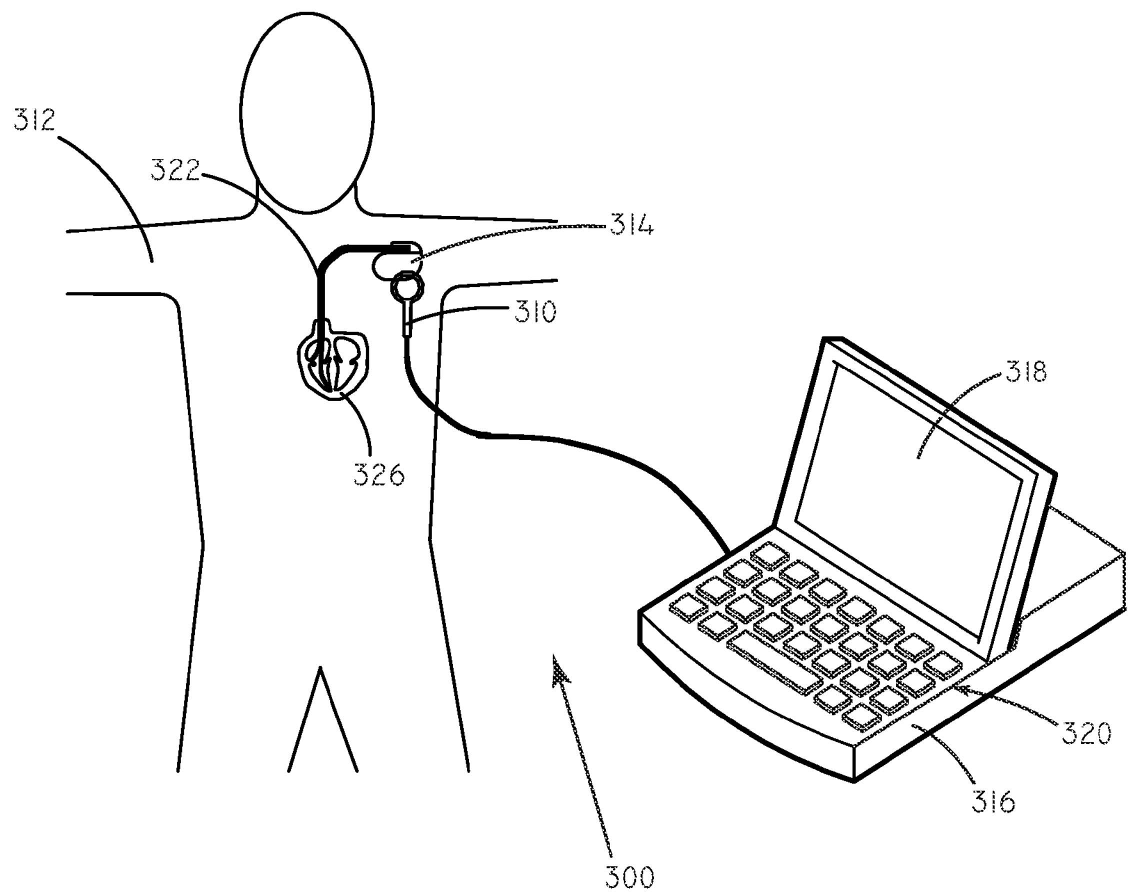
FIG. 3 is a schematic view of an exemplary system consistent with at least one embodiment of the invention.

Embodiments of systems and methods included herein can be used to manage noise in sensed signals including atrial signals. FIG. 3 is a schematic of an exemplary system 300, consistent with at least one embodiment of the invention. The system 300 can include an implantable medical device 314 disposed within a patient 312. The implantable medical device 314 can be of various types such as, for example, a pacemaker, a cardioverter-defibrillator, a cardiac resynchronization device, or the like. One example of an implantable medical device is disclosed in commonly assigned U.S. Pat. No. 4,562,841, the content of which is herein incorporated by reference in its entirety. In some embodiments, the implantable medical device 314 can include one or more leads 322 disposed in or near the patient's heart 326.

The implantable medical device 314 can be in communication with an external medical device 316. In some embodiments, communication between the implantable medical device 314 and the external medical device 316 can be via inductive communication through a wand 310 held on the outside of the patient 312 near the implantable medical device 314. However, in other embodiments, communication can be carried out via radiofrequency transmission, acoustically, or the like.

In some embodiments the implantable medical device 314 can include one or more implantable sensors in order to gather data regarding the patient 312.

The implantable medical device 314 can be configured to store data over a period of time, and periodically communicate with the external medical device 316 in order to transmit some or all of the stored data.

The external medical device 316 can include a video output device, such as a display screen 318 for displaying video output. In some embodiments, the external medical device 316 can be configured to process the gathered data. The external medical device 316 can also include a user input device 320, such as keys. The external medical system 316 can be for example, a programmer/recorder/monitor device, a computer, an advanced patient management system (such as the LATITUDE® Patient Management System), or a personal digital assistant (PDA). Exemplary programmer/recorder/monitor devices include the Model 3120 Programmer, available from Boston Scientific Corporation, Natick, Mass..

Figure 4:
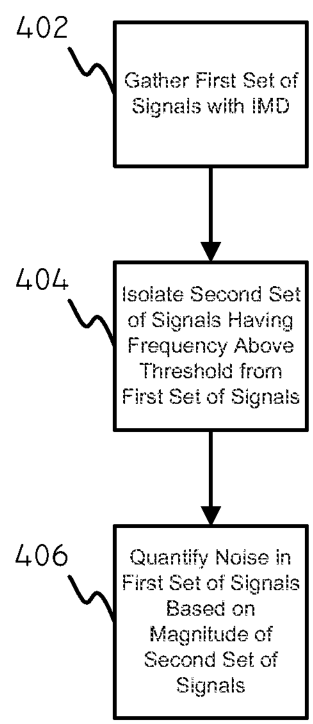
FIG. 4 is a flow chart consistent with at least one embodiment of the invention.

Systems herein can be configured to execute methods that manage noise present in signals. FIG. 4 is a flow chart consistent with at least one embodiment of the invention. In a first operation 402, a system can gather a first set of signals with an implantable medical device. By way of example, an implantable medical device can sense signals and store them for processing. The first set of signals can be a series of samples over a particular time period. By way of example, if the system is trying to assess an atrial evoked response, then the time period can span the atrial evoked response measurement time window. The samples can be effectively connected together and treated as a continuous signal for purposes of analysis. Values from a previous detection window can be used for the initial calculations in the current detection window.

In a second operation 404, the system can filter the first set of signals to produce a second set of signals having a frequency above a cutoff. As such, a subset of the first set of signals can be isolated. This can be done in various ways. In some embodiments, a filter, such as a high pass filter, can be used to isolate the second set of signals. Exemplary methods and filters are described in greater detail below.

In a third operation 406, the system can estimate noise in the first set of signals based on the magnitude of the second set of signals. In other words, the magnitude of the second set of higher-frequency signals can be used as a proxy for the total amount of noise present in the first set of signals. If the estimated noise is too high, then the system can undertake operations to reduce the adverse impact on accuracy that might otherwise happen.

Figure 5:
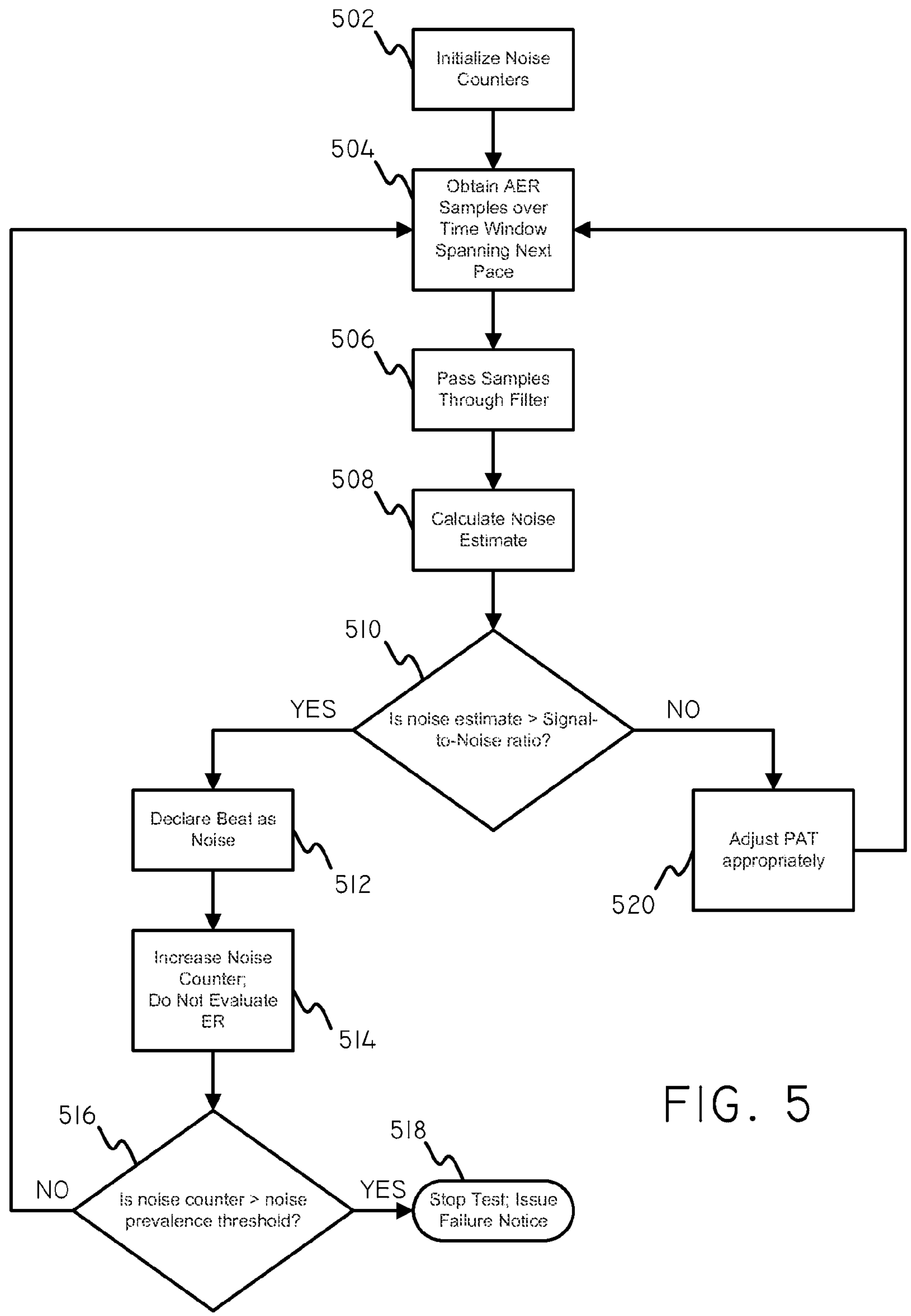
FIG. 5 is a flow chart consistent with at least one embodiment of the invention.

FIG. 5 is a flow chart consistent with at least one embodiment of the invention. In a first operation 502, noise counters can be initialized. The noise counters can be useful in order to track noise behavior over a period of time. In another operation 504, atrial evoked response (AER) samples can be obtained over a particular time window. AER samples are measurements of electrical activity spanning a window of time when contraction would be expected to occur following an electrical stimulation pacing pulse. For example, AER samples can be obtained over a time window including the time immediately following the next delivery of a pacing stimulation pulse from an implantable medical device.

In another operation 506, the samples (first set of signals), can be passed through a filter in order to isolate out the portion (second set of signals) representing a frequency above a particular threshold. As described above, a high pass filter can be used in order to isolate out the second set of signals. In some embodiments, the filter can be a high pass DSP filter. Exemplary filters that can be used include a Butterworth filter, a Chebyshev filter, a Bessel filter or the like. In an exemplary embodiment, the filter is a Chebyshev filter. In some embodiments, the filter can be a high pass Chebyshev filter at 68 Hz.

In another operation 508, the system can calculate a noise estimate. The noise estimate can be generated by processing the second set of signals so as to determine an average or rectified average value. This can be done in various ways. By way of example, in some embodiments, only a specific number of samples around the event of interest (NumSamples) from later in a detection window are used in order to estimate noise. In other words, one or more of the first filtered results making up the second set of electrical signals are not considered in estimating the amount of noise in some embodiments. In some embodiments, zero, one or more of the initial filtered results are not considered in estimating the amount of noise. This approach can allow for time for the filter to settle. In some embodiments, zero, one or more of the initial filtered results are weighed less heavily in estimating noise. In some embodiments the rectified average d(m) can be calculated according to the following formula:

$$d(m) = \left(\frac{CrestFactor}{NumSamples}\right) * \sum_{n-(NumSamples-1)}^{n} |y(n)|$$

where CrestFactor and NumSamples are pseudo-constants and y(n) represents the filter results. In a particular embodiment, CrestFactor can be set to 4 and NumSamples can be set to 24. In some embodiments values for y(n) can be limited to 8 times the previous cycle's noise estimate. In some embodiments, a minimum value can be set for d(m) and if not met then the value for d(m) can be set to that minimum value. By way of example, the minimum value can be set to 80 μV. However, this specific example of calculating a rectified average is only provided by way of illustration and it will be appreciated that the scope of embodiments included herein is not limited to this specific technique. In some embodiments, the rectified average can be further processed. By way of example, in some embodiments the rectified average can be adjusted based on an attack/delay calculation.

In another operation 510, the system can evaluate whether or not the noise estimate exceeds a threshold value for acceptable signal to noise ratio. In some cases, the threshold value for acceptable signal to noise ratio can be preset. In other cases, the threshold value for acceptable signal to noise ratio can be determined dynamically. Regardless, if the noise estimate exceeds the acceptable signal to noise ratio, then the system can declare the samples to represent noise in another operation 512.

In embodiments wherein the system is assessing whether or not capture of the heart chamber has occurred, the ratio can be a capture detection threshold (CDT)-to-noise ratio. Thus, if estimated noise is greater than half of the capture detection threshold, the system will deem the noise to have exceeded the acceptable limit. In some embodiments, the CDT-to-Noise ratio can be set at 2:1. However, this is only one specific example and it will be appreciated that many different ratios could be used.

If the acceptable noise to signal ratio has been exceeded, the system can also increment the noise counter in another operation 514 and not evaluate what might otherwise be treated as an evoked response. For example, even if the magnitude of the first set of signals exceeds the capture detection threshold, the system will not act as if capture has been detected.

In another operation 516, the system can compare the value of the noise counter against a noise prevalence threshold. The noise prevalence threshold can represent how many times the system detects unacceptable levels of noise before the current testing procedure is terminated. If the noise counter value exceeds the noise prevalence threshold, then the test, such as an automatic threshold test, can be terminated and a failure notice can be issued in another operation 518. However, if the noise counter value does not exceed the noise prevalence threshold, then the system can return to operation 504.

If, at operation 510, the noise estimate does not exceed an acceptable signal to noise ratio, the system can proceed with normal evaluation of the evoked response. Optionally, the pace artifact threshold (PAT) can be adjusted in another operation 520. As described above, the pace artifact threshold (PAT) can be used in some algorithms to distinguish between loss of capture and fusion beats. Adjusting the PAT can aid in accurately distinguishing between loss of capture and fusion beats. This is because in many embodiments electrical activity that fails to exceed the PAT are deemed to be indicative of loss of capture. A noise adjusted pace artifact threshold (NPAT) can be calculated using the estimated magnitude of noise. The following formula illustrates one specific example of how to calculate NPAT:

$$\text{Noise Adjusted PAT}(NPAT) = \text{Noise Filter Value}*(1+X)$$

where X is some percentage, such as 50% as one example. The PAT for the next cycle can be set to the greater of starting PAT or NPAT. However, the PAT for the next cycle can be limited by the CDT-to-Noise ratio. Then, after adjusting the pace artifact threshold, the system can return to operation 504.

Figure 6:
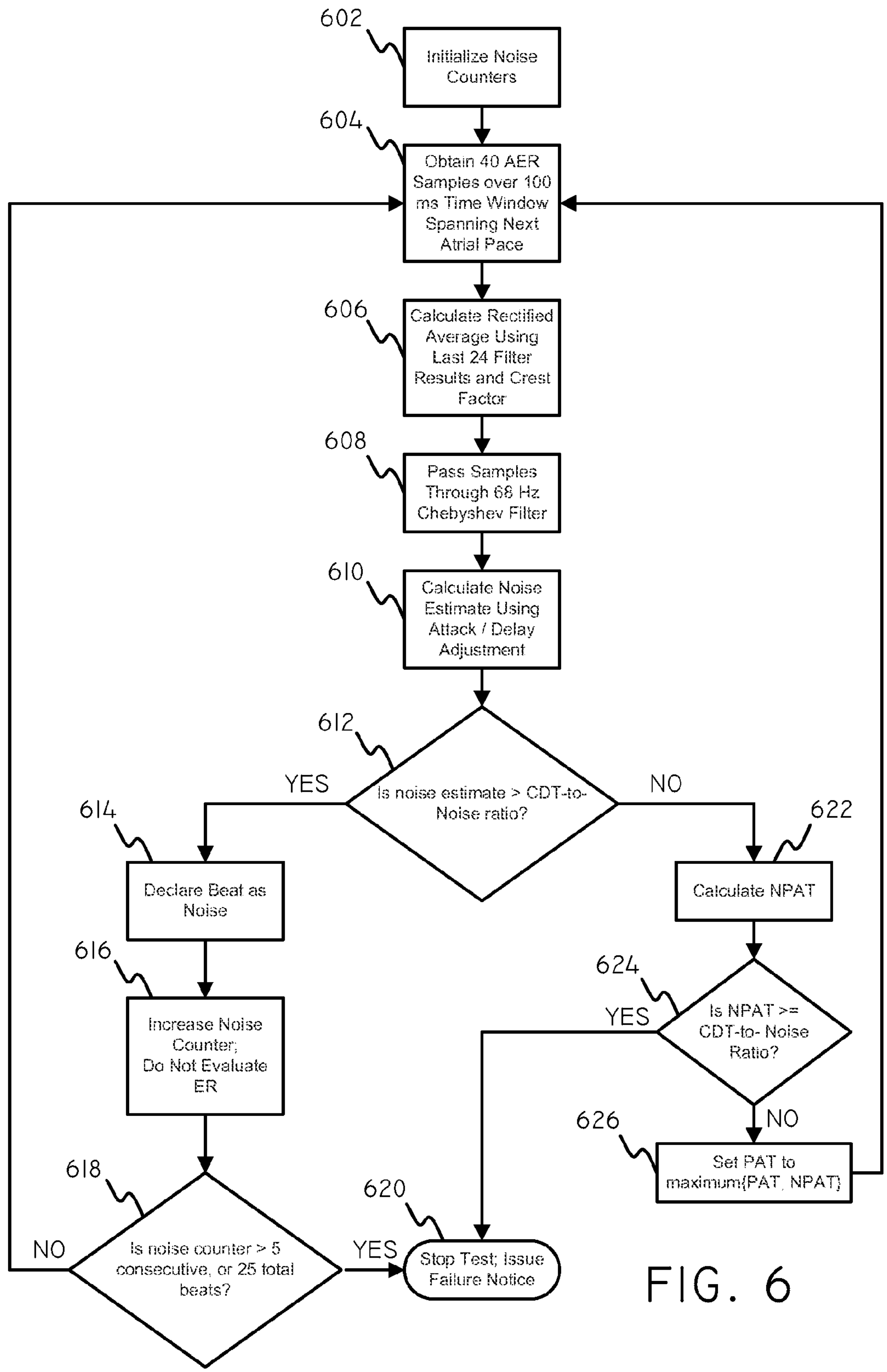
FIG. 6 is a flow chart consistent with at least one embodiment of the invention.

FIG. 6 is a flow chart consistent with at least one embodiment of the invention. In a first operation 602, noise counters can be initialized. In another operation 604, atrial evoked response (AER) samples can be obtained over a particular time window. In this specific embodiment, 40 AER samples over a 100 ms time window spanning the next atrial pace can be obtained, for example, −20 ms to +80 ms with atrial pace at 0 ms. However, it will be appreciated that in other embodiments a different number of samples could be used and/or over a different time window.

In another operation 606, the samples (representing a first set of signals), can be passed through a 68 Hz highpass Chebyshev filter in order to isolate out the portion representing frequencies above a particular cutoff. In another operation 608, a rectified average can be calculated using the last 24 filter results and the crest factor. In another operation 610, the system can optionally calculate a noise estimate using an attack/delay adjustment.

In another operation 612, the system can evaluate whether or not the noise estimate exceeds a preset limit on acceptable signal to noise ratio. If the noise estimate exceeds the acceptable signal to noise ratio, then the system can declare the samples to represent noise in another operation 614. If the samples have been declared to represent noise, then the system can increment the noise counter in another operation 616 and not evaluate what would otherwise be treated as an evoked response.

In another operation 618, the system can compare the value of the noise counter against a noise prevalence threshold. For example, the noise prevalence threshold can be equal to five consecutive beats labeled as noise or twenty five total beats labeled as noise during the testing procedure. However, it will be appreciated that other values can be used besides five and twenty five. In some embodiments, these values can be set by a clinician. If the noise counter value exceeds the noise prevalence threshold, then the automatic threshold test can be terminated and a failure notice can be issued in another operation 620. However, if the noise counter value does not exceed the noise prevalence threshold, then the system can return to operation 604.

If, at operation 610, the noise estimate does not exceed an acceptable signal to noise ratio, the system can proceed with normal evaluation of the evoked response. Optionally, the pace artifact threshold can be adjusted in another operation 622, such as through the technique described above. In operation 624 the system can evaluate whether the NPAT is greater than or equal to the limits of the signal to noise ratio. If the NPAT is greater than the signal to noise ratio, then the automatic threshold test can be terminated and a failure notice can be issued in another operation 620. However, if not, then the pace artifact threshold can be set to the maximum of PAT or NPAT. Then, after adjusting the pace artifact threshold, the system can return to operation 604.

Methods included within the scope herein can be executed by various types of systems. In some embodiments, methods can be executed by an implantable medical device. In other embodiments, methods can be executed by an external device that interfaces with an implantable medical device such as a programmer/recorder/monitor device. In still other embodiments, some method steps can be executed by an implantable medical device while other steps can be executed by an external device.

Figure 7:
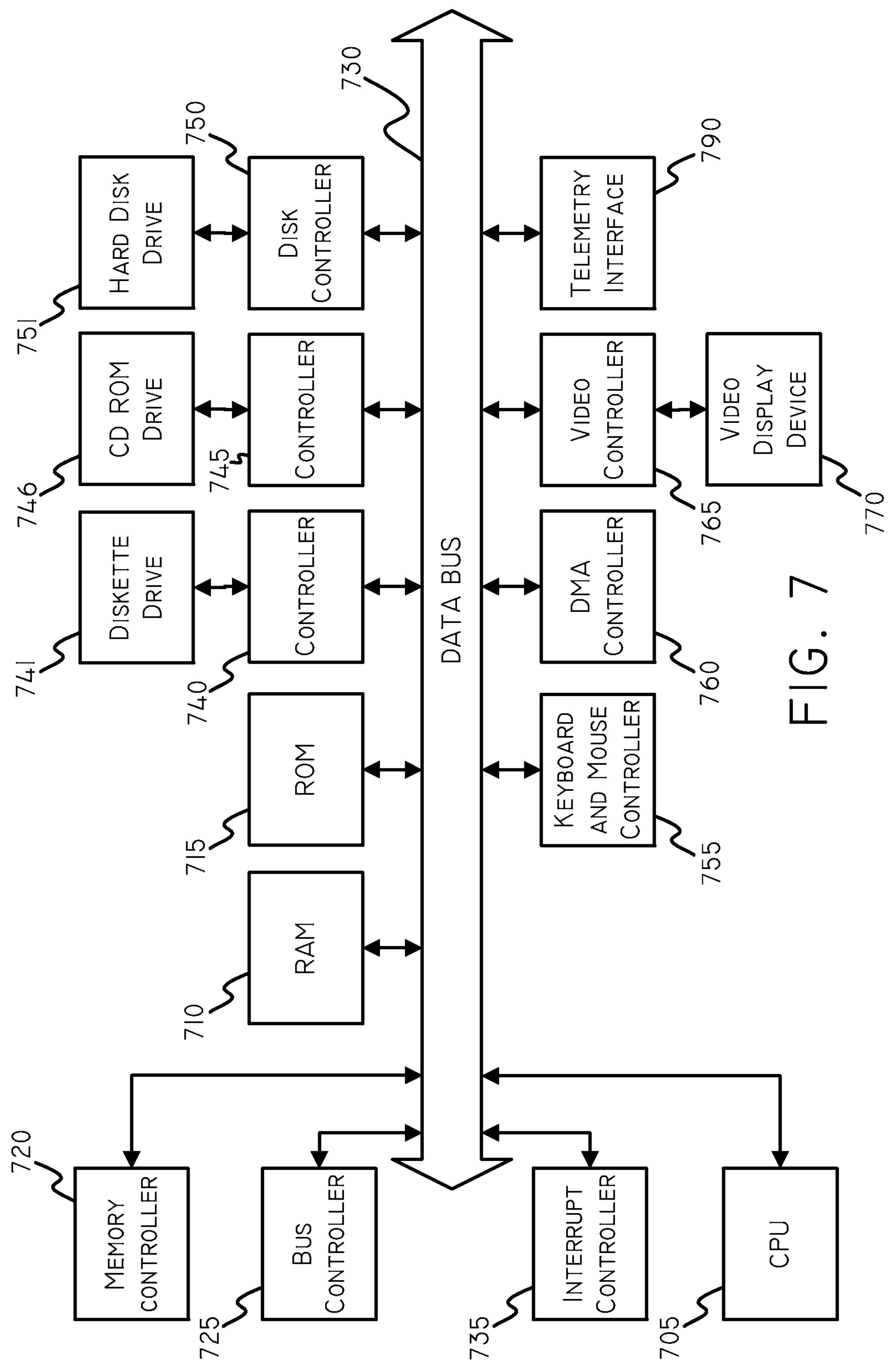
FIG. 7 is a schematic view of components of an external device in accordance with at least one embodiment herein.

Exemplary external devices, such as programmer/recorder/monitors, can include components common to many computing devices. Referring now to FIG. 7, a diagram of various components is shown in accordance with some embodiments of the invention. The external system includes a central processing unit (CPU) 705 or processor circuit, which may include a conventional microprocessor, random access memory (RAM) 710 for temporary storage of information as part of a memory circuit, and read only memory (ROM) 715 for permanent storage of information. A memory controller 720 is provided for controlling system RAM 710. A bus controller 725 is provided for controlling data bus 730, and an interrupt controller 735 is used for receiving and processing various interrupt signals from the other system components.

In some embodiments mass storage can be provided by diskette drive 741, which is connected to bus 730 by controller 740, CD-ROM drive 746, which is connected to bus 730 by controller 745, and hard disk drive 751, which is connected to bus 730 by controller 750. In some embodiments, a USB storage device can be used. User input to the programmer system may be provided by a number of devices. For example, a keyboard and mouse can connected to bus 730 by keyboard and mouse controller 755. DMA controller 760 is provided for performing direct memory access to system RAM 710. A visual display is generated by a video controller 765 or video output, which controls video display 770. The external system can also include a telemetry interface 790 or telemetry circuit which allows the external system to interface and exchange data with an implantable medical device. This description of elements is only provided by way of example and it will be appreciated that some embodiments may lack various elements illustrated in FIG. 7. For example, some embodiments of external devices may lack a diskette drive 741.

Figure 8:
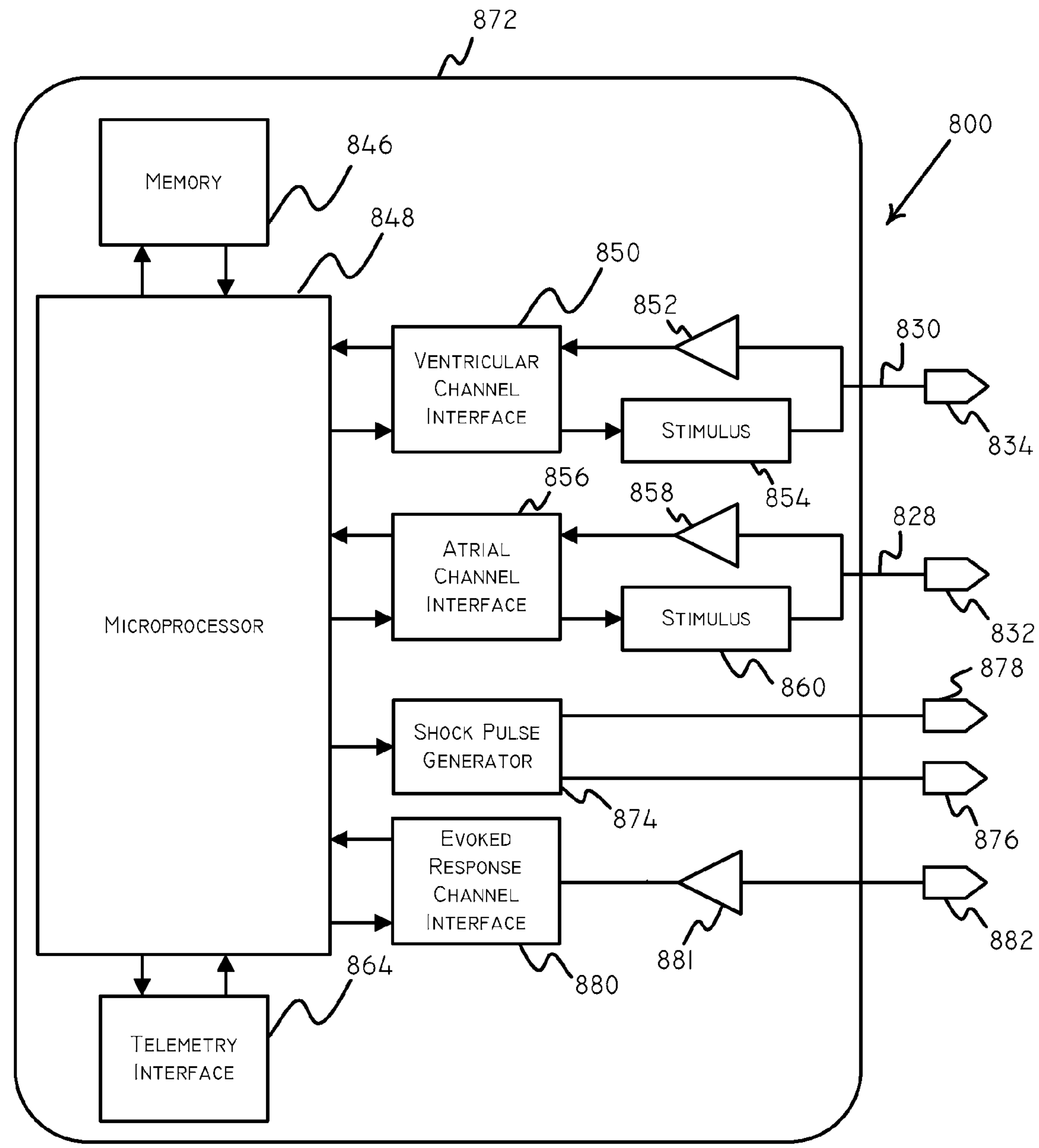
FIG. 8 is a schematic view of components of an implantable medical device in accordance with at least one embodiment herein.

Referring now to FIG. 8, some components of an exemplary implantable device 800 are schematically illustrated. The implantable medical device 800 can include a controller module 872 coupled to one or more stimulation leads 830 and 828. The controller module 872 can include a microprocessor 848 (or processor circuit) that communicates with a memory circuit (or module) 846 via a bidirectional data bus. The memory circuit 846 typically includes ROM or RAM for program storage and RAM for data storage. The controller module 872 can be configured to execute various operations such as processing of signals and execution of methods as described herein. A telemetry interface 864 is also provided for communicating with an external unit, such as a programmer device or a patient management system.

The controller module 872 can include ventricular sensing and pacing channels including sensing amplifier 852, output circuit 854, and a ventricular channel interface 850 which communicates bidirectionally with a port of microprocessor 848. The ventricular sensing and pacing channel can be in communication with stimulation lead 830 and electrode 834.

The controller module 872 can include atrial sensing and pacing channels including sensing amplifier 858, output circuit 860, and an atrial channel interface 856 which communicates bidirectionally with a port of microprocessor 848. The atrial sensing and pacing channel can be in communication with stimulation lead 828 and electrode 832.

For each channel, the same lead and electrode can be used for both sensing and pacing. The channel interfaces 850 and 856 can include analog-to-digital converters for digitizing sensing signal inputs from the sensing amplifiers and registers which can be written to by the microprocessor in order to output pulses, change the pacing pulse amplitude, and adjust the gain and threshold values for the sensing amplifiers.

A shock pulse generator 874 can also be interfaced to the microprocessor for delivering defibrillation shocks to the heart via a separate pair of electrodes 876, 878. In some embodiments, electrodes 876 and 878 can be disposed along stimulation lead 830 and stimulation lead 828 respectively.

The controller module 872 can also include an evoked response channel including an evoked response channel interface 880, evoked response sensing amplifier 881, and electrode 882. The evoked response channel can be used to gather a first set of electrical signals as included with various embodiments herein. The channel interface 880 can include various components, such as filters used with embodiments herein.

In some embodiments, one or more of these components may be omitted. By way of example, if the implantable medical device is a pacemaker, then it may not include a shock pulse generator 874. Similarly, depending on the type of the device and its configuration, it may have a greater or lesser number of electrodes and channels.

Systems and methods of managing noise included herein can have many different applications. As one example, systems and methods included herein can be used in the context of automatic threshold testing, such as right atrial automatic threshold testing. The goal of atrial automatic threshold testing is to automatically determine atrial pacing thresholds using evoked response (ER) sensing. The algorithm can monitor the atrial evoked response (AER) signal following each atrial pacing pulse to determine whether or not the pacing pulse captured the atrium. In some embodiments, the automatic threshold test can begin by pacing the atrium at a high pacing voltage and then periodically reducing the pacing voltage until the atrial pacing threshold (the minimum amplitude required to capture the atrium) is found. The atrial pacing threshold can be the lowest amplitude that does not result in one or more loss of capture events. However, it will be appreciated that systems and methods included herein can be used in other applications beyond automatic threshold testing and are thus not limited to that context. For example, systems and methods included herein can be used in the context of various general automatic testing procedures.

It should be noted that, as used in this specification and the appended claims, the singular forms “a,” “an,” and “the” include plural referents unless the content clearly dictates otherwise. It should also be noted that the term “or” is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method for processing atrial electrical signals obtained from a patient comprising:

gathering a first set of atrial electrical signals within the patient using an implantable medical device during an atrial pacing threshold test, the first set of electrical signals comprising a set of samples of electrical activity from a discrete sample time window spanning a pacing event, wherein the sample time window starts in response to an electrical stimulation p acing pulse;

filtering the first set of atrial signals to provide a second set of electrical signals, the second set of electrical signals comprising frequencies above a cutoff frequency;

estimating the amount of noise present in the first set of atrial electrical signals based on the magnitude of the second set of electrical signals;

calculating a noise threshold value according to a capture detection threshold;

discarding the first set of atrial electrical signals if the estimated amount of noise exceeds the noise threshold value;

calculating an updated noise adjusted pace artifact threshold based on the estimated amount of noise if the noise does not exceed the noise threshold value;

comparing the updated noise adjusted pace artifact threshold to the noise threshold value; and when the updated noise adjusted pace artifact threshold is less than the noise threshold value, classifying the electrical signal as loss of capture or fusion.

2. The method of claim 1, wherein one or more of the initial filtered results making up the second set of electrical signals are not considered in estimating the amount of noise.

3. The method of claim 1, further comprising identifying the first set of electrical signals as indicative of noise if the estimated amount of noise exceeds a threshold value.

4. The method of claim 3, further comprising incrementing a noise counter if the first set of electrical signals is identified to be indicative of noise.

5. The method of claim 4, further comprising terminating an automatic threshold testing procedure if the noise counter exceeds a predetermined value.

6. The method of claim 1, wherein filtering the first set of signals is performed with a Chebyshev high pass filter at 68 Hz.

7. The method of claim 1, the first set of electrical signals comprising a set of samples of atrial myocardial electrical activity taken over a 100 ms time window.

8. The method of claim 1, wherein estimating the amount of noise present in the first set of electrical signals based on the magnitude of the second set of electrical signals comprises calculating a rectified average value for the magnitude of the second set of electrical signals.

9. A medical device comprising: a processor circuit; and a memory circuit operatively connected to the processor circuit; the medical device configured to gather a first set of electrical signals from a patient, the first set of electrical signals comprising a set of samples of electrical activity from a discrete sample time window spanning a pacing event, wherein the sample time window starts in response to an electrical stimulation pacing pulse;

filter the first set of electrical signals to provide a second set of electrical signals, the second set of electrical signals including frequencies above a cut off frequency;

estimate the amount of noise present in the first set of electrical signals based on the magnitude of the second set of electrical signals, wherein one or more of the initial filtered results making up the second set of electrical signals are excluded from the noise estimate;

calculate a noise threshold value according to a capture detection threshold;

discard the first set of electrical signals if the estimated amount of noise exceeds the noise threshold value;

calculate an updated noise adjusted pace artifact threshold based on the estimated amount of noise if the estimated amount of noise does not exceed the noise threshold value;

compare the updated noise adjusted pace artifact threshold to the noise threshold value; and when the updated noise adjusted pace artifact threshold is less than the noise threshold value, classify the electrical signal as loss of capture or fusion.

10. The medical device of claim 9, further configured to identify the first set of electrical signals as indicative of noise if the estimated amount of noise exceeds a threshold value.

11. The medical device of claim 10, further configured to increment a noise counter if the first set of electrical signals is identified as indicative of noise.

12. The medical device of claim 11, further configured to terminate an automatic threshold testing procedure if the noise counter exceeds a threshold value.

13. The medical device of claim 9, further comprising a highpass Cheby shev filter at 68 Hz.

14. The medical device of claim 9, the first set of electrical signals comprising a set of samples of atrial electrical activity taken over a 100 ms time window.

15. The medical device of claim 9, the device further configured to estimate the amount of noise present in the first set of electrical signals based on the magnitude of the second set of electrical signals comprises calculating a rectified average value for the magnitude of the second set of electrical signals.

16. A method for processing electrical signals obtained from a patient comprising:

gathering a first set of electrical signals within the patient using an implantable medical device, the first set of electrical signals comprising a set of samples of electrical activity from a discrete sample time window spanning a p acing event, wherein the sample time window starts in response to an electrical stimulation pacing pulse;

filtering the first set of signals to provide a second set of electrical signals, the second set of electrical signals comprising frequencies above a cutoff frequency;

estimating the amount of noise present in the first set of electrical signals based on the magnitude of the second set of electrical signals;

calculating a noise threshold value according to a capture detection threshold;

discarding the first set of electrical signals if the estimated amount of noise exceeds a noise threshold value;

calculating a noise adjusted pace artifact threshold based on the estimated amount of noise if the noise does not exceed the noise threshold value;

comparing the updated noise adjusted pace artifact threshold to the noise threshold value; and when the up dated noise adjusted pace artifact threshold is less than the noise threshold value, classifying the electrical signal as loss of capture or fusion;

wherein filtering the first set of signals is performed with a Chebyshev high pass filter.

17. The method of claim 16, the first set of electrical signals comprising atrial evoked response samples.

* * * * *